United States Patent
D'Agostino et al.

(10) Patent No.: US 10,188,876 B2
(45) Date of Patent: Jan. 29, 2019

(54) LOCALLY INJECTABLE DOSIMETRIC ORGAN SPACER

(71) Applicant: DOSEVUE NV, Mol (BE)

(72) Inventors: Emiliano D'Agostino, Mol (BE);
Jeroen Hermans, Leuven (BE)

(73) Assignee: DOSEVUE NV, Mol (BE)

( * ) Notice: Subject to any disclaimer, the term of this patent is extended or adjusted under 35 U.S.C. 154(b) by 223 days.

(21) Appl. No.: 15/119,914

(22) PCT Filed: Feb. 13, 2015

(86) PCT No.: PCT/EP2015/053067
§ 371 (c)(1),
(2) Date: Aug. 18, 2016

(87) PCT Pub. No.: WO2015/124499
PCT Pub. Date: Aug. 27, 2015

(65) Prior Publication Data
US 2017/0056689 A1 Mar. 2, 2017

(30) Foreign Application Priority Data
Feb. 18, 2014 (GB) .................................. 1402803.9

(51) Int. Cl.
*A61N 5/10* (2006.01)
*A61K 49/22* (2006.01)
*A61B 6/03* (2006.01)
*A61B 90/00* (2016.01)

(52) U.S. Cl.
CPC ............ *A61N 5/1071* (2013.01); *A61B 6/032* (2013.01); *A61B 90/08* (2016.02); *A61K 49/226* (2013.01); *A61B 2090/0815* (2016.02); *A61N 2005/1094* (2013.01)

(58) Field of Classification Search
CPC . A61B 6/032; A61B 90/08; A61B 2090/0815; A61K 49/226; A61N 5/1071; A61N 2005/1094
USPC ......................................................... 600/431
See application file for complete search history.

(56) References Cited

U.S. PATENT DOCUMENTS

| | | | |
|---|---|---|---|
| 7,744,913 B2 * | 6/2010 | Noyes ..................... | A61K 51/12 424/422 |
| 2004/0236207 A1 | 11/2004 | Widener et al. | |
| 2006/0043314 A1 | 3/2006 | Katzir et al. | |
| 2010/0176343 A1 | 7/2010 | Chen et al. | |
| 2011/0121188 A1 | 5/2011 | Black et al. | |
| 2012/0259197 A1 | 10/2012 | Isham | |
| 2014/0213841 A1 * | 7/2014 | D'Hooge ............... | A61B 8/481 600/1 |
| 2014/0336507 A1 | 11/2014 | Cheng | |

FOREIGN PATENT DOCUMENTS

| | | | |
|---|---|---|---|
| JP | 2008049145 A | 3/2008 | |
| TW | 201347736 A | 12/2013 | |
| WO | 2004000103 A2 | 12/2003 | |
| WO | 2006078770 A2 | 7/2006 | |
| WO | 2013034709 A1 | 3/2013 | |
| WO | WO 2013034709 A1 * | 3/2013 | ............. A61B 8/481 |

OTHER PUBLICATIONS d'Errico, F., et al. "A position-sensitve neutron spectrometer/dosimeter based on pressurized superheated drop (bubble) detectors". Nuclear Instruments and Methods in Physics Research Section A. 2002. pp. 113-118. vol. 476.*
Chapet et al., "Prostate Hypofractionated Radiation Therapy: Injection of Hyaluronic Acid to Better Preserve the Rectal Wall," International Journal of Radiation Oncology Biology Physics, Nov. 13, 2012, pp. 72-76, vol. 86, No. 1.
D'Errico et al., "In Vivo Neutron Dosimetry During High-Energy Bremsstrahlung Radiotherapy," International Journal of Radiation Oncology Biology Physics, Apr. 13, 1998, pp. 1185-1192, vol. 41, No. 5.
D'Errico et al., "A Position-Sensitive Neutron Spectrometer/Dosimeter Based on Pressurized Superheated Drop (Bubble) Detectors," Nuclear Instruments and Methods in Physics Research Section A, 2002, pp. 113-118, vol. 476.
Great Britain Search Report for corresponding Great Britain Application No. 1402803.9, dated May 23, 2014.
International Search Report for corresponding International PCT Application No. PCT/EP2015/053067, dated May 4, 2015.

(Continued)

*Primary Examiner* — Michael Carey
(74) *Attorney, Agent, or Firm* — Workman Nydegger

(57) ABSTRACT

The present invention relates to a system, a method and a filler for measuring a dose of ionizing radiation received by a pre-determined part of the body during radiotherapy while creating a space between the organ to be irradiated and organs to be protected. The invention also relates to uses of such filler. The system comprises an injectable dosimetric filler, which under the influence of ionizing irradiation undergoes measurable physical and/or chemical changes, while preserving its spatial integrity; a detector system for measuring the physical and/or chemical changes within the radiation sensitive filler by sending an energy wave to the radiation sensitive filler and capturing the signal emitted therefrom; and a control unit for processing the signal captured by the detector system and calculating a dose of ionizing radiation previously or simultaneously received by each part of the volume of the radiation sensitive filler on the basis of said signal.

14 Claims, No Drawings

(56) References Cited

OTHER PUBLICATIONS

Kishi et al., "Critical Organ Preservation in Reirradiation Brachytherapy by Injectable Spacer," International Journal of Radiation Oncology Biology Physics, Mar. 3, 2009, pp. 587-594, vol. 75, No. 2.

Porter, "Overview of Some Major Incidents in Radiotherapy and their Consequences," British Institute of Radiology Annual Conference—Radiotherapy Errors and Near Misses, Sep. 2012, pp. 1-14.

* cited by examiner

LOCALLY INJECTABLE DOSIMETRIC ORGAN SPACER

FIELD OF THE INVENTION

The invention relates to the field of radiation therapy. More specifically it relates to a system, method and filler for dosimetry using a minimally invasive organ spacer. The system allows the sparing of organs at risk while also performing in-situ radiation dosimetry, nearby the irradiated tissue. The invention also relates to a device used in said system and method.

BACKGROUND OF THE INVENTION

With an estimated 2.9 million new cases (54% occurring in men, 46% in women) and 1.7 million deaths (56% in men, 44% in women) each year, cancer remains a major public health problem in Europe and the rest of the world. An important modality in any therapeutic cancer strategy is irradiation of the tumor with high energy photons or particles, e.g. by radiotherapy. Developments in radiotherapy treatments have brought solutions that allow a more precise delivery of a higher dose of irradiation to the tumor with fewer side effects to healthy tissues. New techniques, such as tomotherapy and cyberknife, make use of 6 MV photons, while also the use of charged particle beams, i.e. hadrontherapy, plays an increasingly important role, due to their intrinsic high ballistic precision. Hadrontherapy can for example allow the delivery of a very high dose to the target volume, while keeping the dose to the surrounding healthy tissues limited.

The advancement of these treatment techniques is thoroughly related to advances in dosimetry, in order to fully exploit their high tumor conformity.

There are several reported cases of accidents in conventional radiotherapy treatments due to malfunctioning of the equipment, or due to human errors, as can be seen for instance in "Overview of the Major Incidents in Radiotherapy" from Dr. H. Porter, published at the British Institute of Radiology annual conference, 2012.

Unfortunately no on-line in-vivo dosimetry system is systematically in use in the clinical routine nowadays.

Prior art approaches to on-line in-vivo dosimetry, e.g. making use of diodes, MOSFET's (Metal Oxide Semiconductor Field Effect Transistor), diamond detectors, TLD's (Thermoluminescent Dosimeter) or scintillators, perform a dose measurement at the level of the skin while a measurement in-situ, e.g. at the level of the tumor, would be preferable.

In the radiotherapy field, methods are known which enable an in-situ dose assessment using dosimeters that are implanted or inserted into cavities. For example, US2011/121188 discloses a system which comprises internally positioning single-use MOSFET dosimeters in a patient's body to evaluate the radiation dose delivered during a medical procedure or treatment session. The related patent application US2004/236207 discloses positioning single-use adhesive dosimeter patches just onto the skin of a patient. Therefore, the dosage of energy that is planned for, often cannot be measured, determined or monitored very accurately, in the tumor itself or in the surrounding tissues. WO2013/034709 discloses a system for measuring a radiation dose in and around a tumor, during radiotherapy. The system uses gas-filled microbubbles as radio-sensitive agents which undergo measurable and quantifiable changes under the influence of radiation. The quantitative measurements are performed by means of echography. The radiation sensitive microbubbles are systemically administered to the body by injection and distributed with the bloodstream. In particular embodiments, the gas-filled microbubbles may be adapted to comprise at least a binding site to direct them preferentially to the tumor tissue, e.g. by attaching them to a tumor-specific target, e.g. tumor antigen.

In US2010/0176343A1 is described a system for in vivo dosimetry, using energy-transfer nanocomposite materials, which under the influence of ionizing radiation scintillate, emitting luminescence in a particular wavelength interval. The emitted light can be captured and its intensity used as a measure of the intensity of the ionizing radiation. The nanocomposite materials are injected into the tumor or into a blood vessel that supplies the tumor with blood. Occasionally, the nanoparticles can be targeted to the tumor tissue using tumor specific ligands.

In both WO2013/034709 and US2010/0176343A1, functionalization of the particles is needed in order to selectively target the tumor. Furthermore, a critical concentration will be needed in the tumor to be able to generate a significant dosimetric signal.

Yet another known system for in situ dosimetry is based on the use of alanine, which is filled in capsules and placed within body cavities, e.g. within the vagina. Upon irradiation, free radicals are formed which can be detected with Electron Paramagnetic Resonance (EPR). The system has a number of disadvantages, such as relatively low sensitivity, the fact that it is suited for measurements at discrete locations only and that EPR is not a commonly available technique. Moreover, in process measurements are impossible as the capsules have to be removed and brought into the lab for performing the EPR analysis.

When irradiating a tumor, one of the most important factors limiting the dose that can be applied to the tumor, is the dose absorbed by the so called organs at risk, OAR, situated in proximity of the tumor. For instance, in the treatment of prostate cancer, the rectum is an important OAR that should be spared as much as reasonably possible. Dose to OARs can be limited either using an optimized radiation delivering technique (e.g. brachytherapy) or by somehow shielding OARs, or combining both factors. Shielding can be achieved by putting material between the radiation field and the OAR or by pushing the OAR further away from the radiation field.

In WO2006078770A2 an injectable system is described that temporary increases the distance between two tissues/organs in the body. In prostate cancer patients, this system can be used to push the rectum away from the prostate. This system has exclusively a mechanical function and performs no dosimetry measurement. Estimation of the efficacy of such devices is always performed upon completion of the radiotherapy treatment, by looking at the degree of rectal complications. However, it is well known that in some patients, the presence of an internal gas pocket can lead to internal organ movements between two consecutive treatment fractions, therefore modifying the relative distance that was originally created between prostate and rectum. Adding a dosimetric functionality to the spacer gel would definitely help improving patient safety.

SUMMARY OF THE INVENTION

It is an object of embodiments of the present invention to provide efficient systems and methods for minimally invasive in situ radiation dose quantification, whereby measurements can be made in a spatially continuous fashion over one, two or three dimensions, i.e. along a line, over a surface or within a volume, while, at the same time limiting the dose to OARS. From the spatial distribution of irradiation in the measured volume, irradiation doses in adjacent tissues with similar density can be extrapolated and calculated as well.

The above objective is accomplished by a system, method and device according to the present invention.

Although the methods and systems disclosed in the prior art provide useful solutions for performing dosimetry under particular conditions, there still exists a need for an improved system and method for efficiently measuring a radiation dose in and around a tumor, during radiotherapy. Many of the prior-art systems in fact only offer single point measurements, which may be of limited use in a region characterized by a strong dose gradient, or rely upon functionalization, e.g. with antibodies, peptides etc., in order to bring systemically injected dosimetric particles to the tumor. Also, there is a strong need for devices limiting the dose to OAR, e.g. as described in WO2006078770A2. Not only would such devices potentially limit the dose to one or more OARs, but they may also allow the administration of a higher dose to the tumor.

In a first aspect, the present invention provides a system for measuring a radiation dose, e.g. a dose of ionizing irradiation, received by a pre-determined body part, e.g. a pre-determined part of the body, such as a body of a human or animal subject, during a radiotherapy treatment, e.g. during radiotherapy. For example the pre-determined body part may comprise a tissue volume corresponding to an irradiation target volume in an irradiation treatment plan specifically drawn up for the human or animal subject.

The system comprises a) a viscous or semi-solid radiation sensitive filler, e.g. a volume of such radiation sensitive filler, e.g. an injectable volume, adapted for being injected between said predetermined body part and a tissue to be protected from radiation. For example, the system may comprise a medium to be injected in a minimally invasive way between the irradiated part of the body and a tissue that has to be protected from radiation, e.g. an organ at risk. This filler is adapted for undergoing a measurable and quantifiable physical and/or chemical change under the influence of ionizing radiation, for example at least partially caused by ionizing radiation or at least partially induced by ionizing radiation, e.g. at least partially determined by an amount of ionizing radiation locally received in the filler medium. The filler is also adapted for substantially preserving, during the radiotherapy treatment, its initial morphology determined by the shape and volume of the radiation sensitive filler upon injection between said predetermined part of the body and said tissue to be protected, e.g. the filler may be adapted for undergoing this measurable physical and/or chemical change while preserving its initial morphology, e.g. keeping its spatial integrity, for example its shape and volume, over the time, e.g. in order to minimize dose to OAR.

The viscous or semi-solid radiation sensitive filler in accordance with embodiments of the present invention may comprise a viscous or semi-solid medium that is substantially uniformly and substantially continuously radiation sensitive. The radiation sensitive medium may for example be substantially homogeneously and/or uniformly distributed over its volume when injected, e.g. homogeneously and/or uniformly distributed over its confined volume when injected between the irradiated part of the body and the tissue that has to be protected from radiation. Thus, the radiation sensitive medium may advantageously enable measurements to be performed in a spatially continuous fashion over one, two or three spatial dimensions, in which the radiation sensitive medium may allow the selection of a spatial resolution of such measurements independently of the medium, but for example, only by the detector system. For example, such spatial continuity of the medium may advantageously enable a continuous dose measurement in 3D in a tumor, in the OAR and between or substantially around them, e.g. around the predetermined body part and/or the OAR.

The system also comprises b) a detector system adapted for measuring of, e.g. for the mapping and quantification of, the physical and/or chemical change within the radiation sensitive filler by sending an energy wave to the radiation sensitive filler and capturing a signal emitted therefrom, e.g. in response to this energy wave. The detector system may thus be adapted for generating a responsive signal which relates to the dose of ionizing radiation received in each part of the radiation sensitive filler.

For example, the signal may be generated by attenuation, diffraction, refraction, reflection, phase modulation, frequency modulation, excitation and/or other form of transformation of the energy wave in the radiation sensitive medium such as to convey information about the physical and/or chemical change in the properties of this signal. For example, the detector system may be adapted for generating a responsive signal which relates to the dose of ionizing irradiation received in each part of the radiation sensitive medium. The detector system may advantageously enable the acquisition of spatial measurements in a spatially continuous fashion over one, two or three dimensions, e.g. the acquisition of a voxelized volume, a pixelized plane or a pixelized line of spatial measurements, in which the spatial resolution may be independent of the properties of the radiation sensitive medium. In particularly advantageous embodiments, the spatial resolution may even be selected after the physical and/or chemical change within the radiation sensitive medium under the influence of irradiation has occurred.

The system also comprises c) a control unit adapted for processing the captured signal, e.g. the signal captured by the detector system, and for calculating a dose of ionizing radiation previously or simultaneously received by each part of the volume of the radiation sensitive filler taking said signal into account, e.g. on the basis of said response signal. Received by each part of the volume may for example refer to in at least two distinct regions of the confined volume, e.g. in a plurality of locations in said confined volume, for example in a plurality of spatial voxels in said confined volume. The control unit may thus be adapted for calculating a dose of ionizing radiation previously or simultaneously received by each part of the volume of the radiation sensitive medium based on said response signal.

In a system according to embodiments of the present invention, the radiation sensitive filler may comprise a suspension of superheated droplets. In a system according to embodiments of the present invention, the superheated droplets may be encapsulated by a polymeric shell. In a system according to embodiments of the present invention, the superheated droplets may be in a stable state and the droplets may be adapted for re-condensing when switching the radiation source off such as to spontaneously reset said physical and/or chemical change of said radiation sensitive filler. In a system according to embodiments of the present invention, the superheated droplets may be in a metastable state. In a system according to embodiments of the present invention, the radiation sensitive filler may comprise a suspension of gas-filled microbubbles. In a system according to embodiments of the present invention, the detector system may be a CT scanner. In a system according to embodiments of the present invention, the detector system may be an acoustic readout system, such as for instance an ultrasound scanner.

In embodiments of the present invention, the radiation sensitive filler may be adapted for being injected into a natural or surgically created cavity in the body. In embodiments of the present invention, the radiation sensitive medium may be adapted for being injected directly in a tumor and/or in the OAR to be monitored. When the medium is a fluid with appropriate viscosity it may be injected as such.

In embodiments of the present invention, the filler may be adapted for being injected as a fluid material, e.g. highly viscous or semi-solid material, and may be adapted for substantially preserving, during the radiotherapy treatment, its initial morphology by undergoing a further chemical and/or physical change subsequent to the injection, e.g. as the result of an in situ polymerization reaction.

Preferably, the radiation sensitive medium may be a biocompatible, biodegradable viscous fluid (e.g. a viscous gel) in which a radiation sensitive material is dispersed, e.g. emulsified, or dissolved. This medium may comprise a single component medium (e.g. hyaluronic acid or carbopol) or a multi-component medium (e.g. polyethylene glycol as first component and trilysine as second component). In case of multi-component media, the matrix may be liquid when injected and may be adapted for becoming rapidly highly viscous when the different components come into contact and mix. A good viscosity, e.g. a high viscosity, of the medium, when injecting the medium, may be advantageous in order to preserve the spatial distribution of the radiation sensitive material dispersed, e.g. emulsified, or dissolved in the medium.

As radiation sensitive materials in embodiments of the present invention, superheated emulsions may for example be used. Such emulsions may be composed of supercritical droplets composed of a liquid with a relatively low boiling point, such as a perfluorocarbon. The supercritical droplets may be adapted to evaporate when triggered by an external energy contributing event, such as ionizing radiation (such as X-rays, gamma rays, neutrons, alpha, and charged beta particles in general etc.) and the change can be measured by means of, for example, a CT scanner.

The superheated droplets may be suspended as such in a gel medium or they may be encapsulated by a surfactant or polymeric shell, such as e.g. dextran or hyaluronic acid. The droplets may be in a stable or in a metastable state.

In embodiments of the invention, gas-filled microparticles, as described in PCT/EP2012/067539, which is incorporated herein by reference, may be used. Under the influence of ionizing radiation, the physical and chemical properties of the microparticles undergo changes which may be detected and quantified by means of acoustic methods, such as for instance, the present invention, however, not being limited thereto, ultrasound. Preferably said parameters comprise one or more parameters selected from the group consisting of phase velocity, attenuation and nonlinearity. Measurements are performed by directing an energy wave that comprises emitting an ultrasonic or RF wave and detecting a response signal comprises detecting and quantifying the ultrasonic or RF response signal.

Determining the radiation dose may comprise determining a spatial distribution, i.e. a volumetric distribution, of the radiation dose.

In a second aspect, the invention comprises a method for measuring a dose of ionizing irradiation received by a pre-determined body part during a radiotherapy treatment. This method comprises a) sending an energy wave to a viscous or semi-solid radiation sensitive filler. This viscous or semi-solid radiation sensitive filler is pre-injected between the predetermined body part and a tissue to be protected from radiation, e.g. pre-injected in the neighbourhood of irradiated tissue. The radiation sensitive filler is adapted for undergoing a measurable physical and/or chemical change under the influence of ionizing irradiation and for substantially preserving, during said radiotherapy treatment, its initial morphology determined by the shape and volume of said radiation sensitive filler after being pre-injected between the predetermined part of the body and the tissue to be protected. The method also comprises b) capturing, e.g. by a detector system, a signal emitted by the radiation sensitive medium elicited by the energy wave. The emitted signal has characteristics that reflect the physical and/or chemical change. The method also comprises c) processing the captured signal, e.g. in a control unit, and calculating the dose of ionizing irradiation, e.g. in the control unit, previously or simultaneously received by each part of the radiation sensitive filler taking the signal into account. Thus, embodiments of the invention may comprise a method of measuring a dose of ionizing radiation received at a given location within or near tumor tissue, e.g. using a system as described hereinabove.

In a third aspect, the present invention relates to a radiation sensitive filler for measuring a dose of ionizing irradiation received by a pre-determined body part during a radiotherapy treatment. The radiation sensitive filler is a viscous or semi-solid radiation sensitive filler adapted for being injected between the predetermined body part and a tissue to be protected from radiation. The radiation sensitive filler is also adapted for undergoing a measurable physical and/or chemical change under the influence of ionizing irradiation and for substantially preserving, during the radiotherapy treatment, its initial morphology determined by the shape and volume of the radiation sensitive filler upon injection between the predetermined part of the body and the tissue to be protected. The radiation sensitive filler is furthermore adapted for emitting a signal when this signal is elicited by an energy wave, whereby this emitted signal has characteristics that reflect the physical and/or chemical change.

The radiation sensitive filler according to embodiments of the present invention may comprise a viscous medium having liquid droplets dispersed therein. The radiation sensitive filler according to embodiments of the present invention may comprise a suspension of gas-filled microbubbles. The radiation sensitive filler according to embodiments of the present invention may be biocompatible and biodegradable.

In embodiments of the present invention, the radiation sensitive medium may comprise superheated droplets which under the influence of ionizing radiation undergo a phase transition which can be measured by means of CT imaging.

In embodiments of the present invention the radiation sensitive medium may comprise gas-filled microbubbles which under the influence of ionizing radiation undergo physical and/or chemical changes which can be measured by means of an acoustic readout system. In embodiments of the present invention, the acoustic readout system may be standard clinical ultrasound imaging equipment. The acoustic readout system then is adapted to interrogate the microbubbles after they are formed. In alternative embodiments, the acoustic readout system may be of a different type, and may be adapted to listen to the formation of bubbles and to localize events occurring.

In embodiments of the present invention, the concentration of droplets in the viscous medium may be high enough to change the average density of a voxel of medium, upon vaporization of the droplets (initially in a liquid state). The average voxel density may change from 100%, the initial density (water equivalent liquid droplet), down to max. 0.4764 ID+0.5236 VDD, where ID is the initial density and VDD is the vaporized droplet density. The overall shape and volume of the filler may be substantially constant after injection, even after the irradiation.

In embodiments of the present invention, the droplets may have an initial size between 10 nm and 1 μm so that, upon radiation triggered vaporization, they will form gas bubbles with a radius in the order of few μm. The latter have a resonance frequency in a range between 1 and 10 MHz and are easily measurable with an acoustic readout system such as e.g. a clinical ultrasound scanner. Before radiation induced vaporization, the liquid droplets may not be visible either with a CT scan or with an acoustic readout system such as an ultrasound device.

In embodiments of the present invention, the droplets may be stable or metastable. Stable droplets may re-condensate upon termination of the irradiation, resulting in a spontaneous reset of the system.

The present invention also relates to the use of a radiation sensitive filler according to the third aspect of the present invention in radiotherapy of the prostate, wherein the radiation sensitive filler is placed in the potential space between the prostate and the rectum in order to reduce irradiation of the rectum.

The present invention also relates to the use of a radiation sensitive filler according to the third aspect of the present invention in cervical cancer radiotherapy, wherein the radiation sensitive filler is placed in the vagina or cervix in order to reduce irradiation of the rectum.

The present invention also relates to the use of a radiation sensitive filler according to the third aspect of the present invention in paraspinal, sacral or pelvic radiotherapy, wherein the radiation sensitive filler is used to push a bowel and/or at least one kidney away from the irradiation field such as to protect said bowel and/or said at least one kidney from excessive irradiation.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

DETAILED DESCRIPTION OF ILLUSTRATIVE EMBODIMENTS

The present invention will be described with respect to particular embodiments but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In a first aspect, the present invention provides a system for measuring a radiation dose, e.g. a dose of ionizing irradiation, received by a pre-determined body part, e.g. a pre-determined part of the body, such as a body of a human or animal subject, during a radiotherapy treatment, e.g.

during radiotherapy. For example the pre-determined body part may comprise a tissue volume corresponding to an irradiation target volume in an irradiation treatment plan specifically drawn up for the human or animal subject.

The system comprises a) a viscous or semi-solid radiation sensitive filler, e.g. a volume of such radiation sensitive filler, e.g. an injectable volume, adapted for being injected between said predetermined body part and a tissue to be protected from radiation. For example, the system may comprise a medium to be injected in a minimally invasive way between the irradiated part of the body and a tissue that has to be protected from radiation, e.g. an organ at risk. This filler is adapted for undergoing a measurable and quantifiable physical and/or chemical change under the influence of ionizing radiation, for example at least partially caused by ionizing radiation or at least partially induced by ionizing radiation, e.g. at least partially determined by an amount of ionizing radiation locally received in the filler medium. The filler is also adapted for substantially preserving, during the radiotherapy treatment, its initial morphology determined by the shape and volume of the radiation sensitive filler upon injection between said predetermined part of the body and said tissue to be protected, e.g. the filler may be adapted for undergoing this measurable physical and/or chemical change while preserving its initial morphology, e.g. keeping its spatial integrity, for example its shape and volume, over the time, e.g. in order to minimize dose to OAR.

This radiation sensitive medium may for example be substantially homogeneously and/or uniformly distributed over its volume when injected, e.g. homogeneously and/or uniformly distributed over its confined volume when injected between the irradiated part of the body and the tissue that has to be protected from radiation. Thus, the radiation sensitive medium may advantageously enable measurements to be performed in a spatially continuous fashion over one, two or three spatial dimensions, in which the radiation sensitive medium may allow the selection of a spatial resolution of such measurements independently of the medium, but for example, only by the detector system. For example, such spatial continuity of the medium may advantageously enable a continuous dose measurement in 3D in a tumor, in the OAR and between or substantially around them, e.g. around the predetermined body part and/or the OAR.

The system also comprises b) a detector system adapted for measuring of, e.g. for the mapping and quantification of, the physical and/or chemical change within the radiation sensitive filler by sending an energy wave to the radiation sensitive filler and capturing a signal emitted therefrom, e.g. in response to this energy wave. The detector system may thus be adapted for generating a responsive signal which relates to the dose of ionizing radiation received in each part of the radiation sensitive filler.

For example, the signal may be generated by attenuation, diffraction, refraction, reflection, phase modulation, frequency modulation, excitation and/or other form of transformation of the energy wave in the radiation sensitive medium such as to convey information about the physical and/or chemical change in the properties of this signal. For example, the detector system may be adapted for generating a responsive signal which relates to the dose of ionizing irradiation received in each part of the radiation sensitive medium. The detector system may advantageously enable the acquisition of spatial measurements in a spatially continuous fashion over one, two or three dimensions, e.g. the acquisition of a voxelized volume, a pixelized plane or a pixelized line of spatial measurements, in which the spatial resolution may be independent of the properties of the radiation sensitive medium. In particularly advantageous embodiments, the spatial resolution may even be selected after the physical and/or chemical change within the radiation sensitive medium under the influence of irradiation has occurred.

The system also comprises c) a control unit adapted for processing the captured signal, e.g. the signal captured by the detector system, and for calculating a dose of ionizing radiation previously or simultaneously received by each part of the volume of the radiation sensitive filler taking said signal into account, e.g. on the basis of said response signal. Received by each part of the volume may for example refer to in at least two distinct regions of the confined volume, e.g. in a plurality of locations in said confined volume, for example in a plurality of spatial voxels in said confined volume. The control unit may thus be adapted for calculating a dose of ionizing radiation previously or simultaneously received by each part of the volume of the radiation sensitive medium based on said response signal.

In a system according to embodiments of the present invention, the radiation sensitive filler may comprise a suspension of superheated droplets. In a system according to embodiments of the present invention, the superheated droplets may be encapsulated by a polymeric shell. In a system according to embodiments of the present invention, the superheated droplets may be in a stable state and the droplets may be adapted for re-condensing when switching the radiation source off such as to spontaneously reset said physical and/or chemical change of said radiation sensitive filler. In a system according to embodiments of the present invention, the superheated droplets may be in a metastable state. In a system according to embodiments of the present invention, the radiation sensitive filler may comprise a suspension of gas-filled microbubbles. In a system according to embodiments of the present invention, the detector system may be a CT scanner. In a system according to embodiments of the present invention, the detector system may be an acoustic readout system such as an ultrasound scanner.

In embodiments of the present invention, the radiation sensitive filler may be adapted for being injected into a natural or surgically created cavity in the body. In embodiments of the present invention, the radiation sensitive medium may be adapted for being injected directly in a tumor and/or in the OAR to be monitored. When the medium is a fluid with appropriate viscosity it may be injected as such.

In embodiments of the present invention, the filler may be adapted for being injected as a fluid material, e.g. highly viscous or semi-solid material, and may be adapted for substantially preserving, during the radiotherapy treatment, its initial morphology by undergoing a further chemical and/or physical change subsequent to the injection, e.g. as the result of an in situ polymerization reaction.

Preferably, the radiation sensitive medium may be a biocompatible, biodegradable viscous fluid (e.g. a viscous gel) in which a radiation sensitive material is dispersed, e.g. emulsified, or dissolved. This medium may comprise a single component medium (e.g. hyaluronic acid or carbopol) or a multi-component medium (e.g. polyethylene glycol as first component and trilysine as second component). In case of multi-component media, the matrix may be liquid when injected and may be adapted for becoming rapidly highly viscous when the different components come into contact and mix. A good viscosity, e.g. a high viscosity, of the medium, when injecting the medium, may be advantageous in order to preserve the spatial distribution of the radiation sensitive material dispersed, e.g. emulsified, or dissolved in the medium.

As radiation sensitive materials for embodiments of the present invention may be used materials which undergo quantifiable physical or chemical changes under the influence of ionizing radiation, including gamma radiation, X-rays, alpha particles, neutrons, beta particles and charged particles in general. Viscosity of the radiation sensitive medium may also advantageously contribute to the preservation its spatial integrity during irradiation, so that when it is used to move an OAR away from the tumor, the initial distance is kept, while also providing a 3D dose measurement between tumor and OAR, thanks to the radiation sensitive material dispersed in the medium.

As a consequence of exposure to ionizing radiation, the physical and/or chemical properties of the material are modified in such a way that these changes can be recorded non-invasively is situ, using e.g. an acoustic readout system such as for instance a clinical ultrasound system, and/or a clinical digital radiography system (or a CT scanner) or an MRI scanner.

As radiation sensitive materials in embodiments of the present invention, superheated emulsions may for example be used. Such emulsions may be composed of supercritical droplets composed of a liquid with a relatively low boiling point, such as a perfluorocarbon. The supercritical droplets may be adapted to evaporate when triggered by an external energy contributing event, such as ionizing radiation (such as X-rays, gamma rays, neutrons, alpha and beta particles etc.) and the change can be measured by means of, for example, a CT scanner.

The superheated droplets may be suspended as such in a gel medium or they may be encapsulated by a surfactant or polymeric shell, such as e.g. dextran or hyaluronic acid. The droplets may be in a stable or in a metastable state.

In embodiments of the invention, gas-filled microparticles, as described in PCT/EP2012/067539, which is incorporated herein by reference, may be used. Under the influence of ionizing radiation, the physical and chemical properties of the microparticles undergo changes which may be detected and quantified by means of an acoustic readout method and system, for instance ultrasound. Preferably said parameters comprise one or more parameters selected from the group consisting of phase velocity, attenuation and nonlinearity. Measurements are performed by directing an energy wave that comprises emitting an ultrasonic or RF wave and detecting a response signal comprises detecting and quantifying the ultrasonic or RF response signal.

Preferably determining the radiation dose includes determining a spatial distribution, i.e. a volumetric distribution, of the radiation dose.

The control unit may be equipped for calculating a dose of ionizing radiation received throughout the volume of the radiation sensitive medium. The control unit may capture the response signal received or generated by the detection system and transform it in a numerical or graphical dataset which reflects the dose of irradiation received at different locations within the volume of the radiation sensitive medium. By comparing the dose determined this way with the planned dose in the treatment protocol, adaptations can be made which allow optimization of the procedure, i. e. maximization of the dose to the tumor and minimization of the dose to OAR at the same time.

Compared with systems that use systemically injected targeted radiation sensitive materials, such as described in WO2013/034709 or US2010/0176343A1, a system according to embodiments of the invention may have the advantage of providing a more stable localization and concentration of the radiation sensitive material in the organs or tissue or regions that has to be monitored. Indeed, systemically injected particles are subject to, sometimes rapid, elimination or redistribution, necessitating repeated re-calibration.

Compared with inserted single point sensors like MOSFETS, a system according to embodiments of the invention may have the advantage that measurements can be performed in a spatially continuous and uninterrupted fashion in three dimensions. This allows the identification and quantification of radiation gradients within or near the tumor, along a line, over a given surface or within a three-dimensional volume. This may be especially useful in combination with brachytherapy, where radiation gradients near the inserted seeds or needles can be very steep.

When using superheated droplets or gas-filled microbubbles as radiation sensitive materials, the cumulated effect of ionizing radiation is measured. Compared with systems which measure a radiation intensity at a given point in time only, as is the case with MOSFETs, diodes or scintillation luminescence particles, there is no need to perform measurements continuously in order to determine the cumulative dose of radiation received. Hence, the radiation sensitive medium itself acts as a memory that keeps a record of the total dose of irradiation received at any point in time.

Depending on the type of treatment, the filler can stay in place only for a few minutes (e.g. in IORT applications) or for several days (e.g. in brachytherapy or external radiotherapy). After each fraction of irradiation, dosimetry may be performed. This may for example be achieved by acquiring images based on acoustic waves, for instance ultrasound images, and/or radiography images of the radiation sensitive medium and quantifying the change, e.g. in attenuation, obtained as a result of exposure of the radiation sensitive medium to ionizing radiation. A biocompatible, biodegradable radiation sensitive medium according to embodiments may be adapted for being eliminated by the body after the entire treatment will be completed. The spatial resolution of the measurements may depend on the radiation sensitive material used and on the nature of the imaging device used, whereby the resolution of a CT scan is in general higher than that of an acoustic readout system such as ultrasound.

Differences between the actual delivered dose, as recorded by the device, and the calculated dose can therefore be detected and corrected in time. For example, for patients undergoing single IORT treatment with doses of about 20 Gy, online measurements can be foreseen in order to adapt the treatment where needed, in an almost real-time fashion. For patients undergoing multiple brachytherapy fractions, receiving typically doses of about 5 Gy per fraction and twice a day, a close check can be performed after each fraction, so that the treatment can be adapted if needed. In this way a fully adaptive treatment can be achieved.

In a second aspect, the invention comprises a method for measuring a dose of ionizing irradiation received by a pre-determined body part during a radiotherapy treatment. This method comprises a) sending an energy wave to a viscous or semi-solid radiation sensitive filler. This viscous or semi-solid radiation sensitive filler is pre-injected between the predetermined body part and a tissue to be protected from radiation, e.g. pre-injected in the neighbourhood of irradiated tissue. The radiation sensitive filler is adapted for undergoing a measurable physical and/or chemical change under the influence of ionizing irradiation and for substantially preserving, during said radiotherapy treatment, its initial morphology determined by the shape and volume of said radiation sensitive filler after being pre-injected between the predetermined part of the body and the tissue to be protected. The method also comprises b) capturing, e.g. by a detector system, a signal emitted by the radiation sensitive medium elicited by the energy wave. The emitted signal has characteristics that reflect the physical and/or chemical change. The method also comprises c) processing the captured signal, e.g. in a control unit, and calculating the dose of ionizing irradiation, e.g. in the control unit, previously or simultaneously received by each part of the radiation sensitive filler taking the signal into account. Thus, embodiments of the invention may comprise a method of measuring a dose of ionizing radiation received at a given location within or near tumor tissue, e.g. using a system as described hereinabove.

In a third aspect, the present invention relates to a radiation sensitive filler for measuring a dose of ionizing irradiation received by a pre-determined body part during a radiotherapy treatment. The radiation sensitive filler is a viscous or semi-solid radiation sensitive filler adapted for being injected between the predetermined body part and a tissue to be protected from radiation. The radiation sensitive filler is also adapted for undergoing a measurable physical and/or chemical change under the influence of ionizing irradiation and for substantially preserving, during the radiotherapy treatment, its initial morphology determined by the shape and volume of the radiation sensitive filler upon injection between the predetermined part of the body and the tissue to be protected. The radiation sensitive filler is furthermore adapted for emitting a signal when elicited by an energy wave, wherein the emitted signal has characteristics that reflect the physical and/or chemical change.

The radiation sensitive filler according to embodiments of the present invention may comprise a viscous medium having liquid droplets dispersed therein. The radiation sensitive filler according to embodiments of the present invention may comprise a suspension of gas-filled microbubbles. The radiation sensitive filler according to embodiments of the present invention may be biocompatible and biodegradable.

The present invention also relates to the use of a radiation sensitive filler according to the third aspect of the present invention in radiotherapy of the prostate, wherein the radiation sensitive filler is placed in the potential space between the prostate and the rectum in order to reduce irradiation of the rectum.

The present invention also relates to the use of a radiation sensitive filler according to the third aspect of the present invention in cervical cancer radiotherapy, wherein the radiation sensitive filler is placed in the vagina or cervix in order to reduce irradiation of the rectum.

The present invention also relates to the use of a radiation sensitive filler according to the third aspect of the present invention in paraspinal, sacral or pelvic radiotherapy, wherein the radiation sensitive filler is used to push a bowel and/or at least one kidney away from the irradiation field such as to protect said bowel and/or said at least one kidney from excessive irradiation.

In a preferred embodiment, the radiation sensitive medium may comprise superheated droplets which under the influence of ionizing radiation undergo a phase transition which can be measured by means of CT imaging.

In an alternative embodiment, the radiation sensitive medium may comprise gas-filled microbubbles which under the influence of ionizing radiation undergo physical and/or chemical changes which can be measured by means of an acoustic readout system, such as for instance standard clinical ultrasound imaging equipment.

In a preferred embodiment, the concentration of droplets in the viscous medium may be high enough to change the average density of a voxel of medium, upon vaporization of the droplets (initially in a liquid state). The average voxel density may change from 100%, the initial density (water equivalent liquid droplet), down to max. 0.4764 ID+0.5236 VDD, where ID is the initial density and VDD is the vaporized droplet density. The overall shape and volume of the filler may be substantially constant after injection, even after the irradiation.

In another preferred embodiment, the droplets may have an initial size between 10 nm and 1 μm so that, upon radiation triggered vaporization, they will form gas bubbles with a radius in the order of few μm. The latter have a resonance frequency in a range between 1 and 10 MHz and are easily measurable with an acoustic readout system, such as for instance a clinical ultrasound scanner. Before radiation induced vaporization, the liquid droplets may not be visible either with a CT scan or with an acoustic imaging device such as an ultrasound device.

The droplets in embodiments of the present invention may be stable or metastable. Stable droplets may re-condensate upon termination of the irradiation, resulting in a spontaneous reset of the system. The boiling temperature of metastable droplets is typically much lower than body temperature. It is nonetheless possible to disperse them in liquid form in a matrix and keep them liquid at body temperature. The phase transition to gas bubbles may then be triggered by an energy source, such as radiation. Once vaporized, metastable droplets may not revert to liquid form, unless temperature and/or pressure are adapted.

While acting as an in situ dosimetry device, in a preferred embodiment, the radiation sensitive medium may act at the same time as a spacer or filler, increasing the distance between the tissue to be irradiated and the OAR. For example, when the prostate is the organ to be irradiated, the rectum is the main OAR. Radiation damage to the rectum may be decreased by introducing a spacer between the prostate and the rectum, more particularly by inserting the spacer in the potential space between the fascia propria of the rectum and the Denonvilliers' fascia, as described in patent application WO2006/078770, which is incorporated herein by reference. The insertion of the dosimetric gel may for example create a stable volume between prostate and rectum by pushing the latter further away. Because of this increased distance, it is therefore possible to increase the radiation dose imparted to the tumor (located in the prostate) while keeping the dose to the rectum within a safe level. The dosimetric properties of the spacer gel allows 3D dose mapping between rectum and prostate, to make sure that the planned dose gradients is also delivered, without excessive damage to healthy tissues.

In another preferred embodiment, the dosimetric filler can be used to move the bowel and the kidneys away from the treatment field, in the irradiation of paraspinal and sacral/pelvic tumor. In both cases, the dosimetric filler limits the dose to the OAR's and also allows dose monitoring between the tumor and the OAR's.

Hereinbelow, examples are provided in order to further support embodiments of the present invention. However, these examples are intended to illustrate and should not be construed to limit the scope of the invention.

Example 1: A Prostate Cancer Patients is Treated with External Radiotherapy

Before starting treatment, a viscous gel containing liquid superheated droplets, with a radius in the order of 0.1 μm.

The matrix wherein the droplets are dispersed contains hyaluronic acid as a thickening agent. Viscosity of the gel can be in the range between 2000 and 550000 cPoise (without being limitative), depending on how long the gel has to keep in place and on injectability and preferably between 250000 and 550000 cP for long duration in-situ stability. The gel is injected in the space between prostate and rectum, as also described in WO2006078770A2. Differently from WO2006078770A2, the injected gel will not only increase the space between rectum and prostate, but also provide a 3D map of the dose imparted from prostate towards the rectum, therefore helping monitoring the maximal dose to the rectum, while at the same time limiting the dose to the rectum The injected dosimetric gel will keep in place for several weeks and will then be metabolized by the body. Treatment typically consists of 36 irradiation days, with daily doses of 2 Gy.

Upon exposure to radiation, the superheated droplets evaporate, generating gas bubbles inside the viscous gel. The bubbles have a mean diameter of several μm and are locally "frozen" by the viscous gel. As such they can be imaged using conventional clinical ultrasound scanners. In fact the amplitude of the backscattered signal is proportional to the gas bubbles concentration with the gel. Also, that fact that gas bubbles have a non-linear acoustic behavior, will result is a resonance peak of the spectrum of the received ultrasound signal. This resonance peak will only appear upon exposure of the gel to ionizing radiation.

After dose exposure, an ultrasound clinical scanner is used to perform imaging of the gel. The intensity of the resonance peak of the measured ultrasound signal, proportional to the bubbles concentration, gives information on the absorbed dose. This way a correct monitoring of the dose to critical organs can be carried out eventually resulting in an optimized treatment. Dose monitoring after several radiation treatment fractions will result in an increased amplitude of the resonance peak of the injected gel.

The gel system can be calibrated in a standard laboratory using a Co-60 source, in air kerma conditions. A calibration coefficient in terms of number of bubbles/Gy is then used to convert the number of bubbles to absorbed dose.

Example 2: Cervical Cancer

In this second example, we consider a cervical cancer patient, being treated with Ir-192 Pulsed Dose Rate, PDR, brachytherapy. In such treatment, Ir-192 sources are introduced in the patient using a vaginal applicator. The applicator, inserted under anesthesia, is kept in place for several days. At regular intervals, according to the protocol, Ir-192 sources are loaded into the applicator and a radiation pulse is administered to the patient. In these patients a gel can be injected to move the rectum further away from the irradiation region. The gel considered in this example contains a high concentration of dispersed liquid droplets. The gel matrix is composed of hyaluronic acid and it hosts droplets of HFR-134a. Upon exposure to ionizing radiation, these droplets evaporate, turning into gas bubbles. The gel holds its initial morphology over the treatment time.

This phase transition changes the local electronic density of the gel and can therefore be measured with a CT scan. The attenuation coefficient, depending on the local electronic density, is derived from the CT scan and allows a 3D dose reconstruction. More precisely the absorbed dose can be quantified by comparing the change in electronic density before and after irradiation. Using the calibration curve of the CT scanner (Hounsfield units versus electronic density), it is possible to convert the gray value read in each voxel of the CT scan (i.e. its Hounsfield number) into an (electronic) density. The average voxel density will change from 100% the initial density (water equivalent liquid droplets dispersed in the hyaluronic matrix) down to max. 0.4764 ID+0.5236 VDD, where ID is the initial density and VDD is the vaporized droplet density. In fact, in the ideal case that vaporized droplets (i.e. gas bubbles) are completely filling a cubical voxel, it can be shown that the ration between the volume of the bubbles and the voxel volume is equal to 0.5236.

The invention claimed is:

1. A system for measuring a dose of ionizing irradiation received by a pre-determined body part during a radiotherapy treatment, the system comprising:
    a) a viscous or semi-solid radiation sensitive filler adapted for being injected between said predetermined body part and a tissue to be protected from radiation, wherein the radiation sensitive filler is adapted for undergoing a measurable physical and/or chemical change under the influence of ionizing irradiation and for substantially preserving, during said radiotherapy treatment, its initial morphology in order to minimize dose to the tissue to be protected from radiation, the initial morphology being determined by the shape and volume of said radiation sensitive filler upon injection between said predetermined part of the body and said tissue to be protected;
    b) a detector system adapted for measuring said physical and/or chemical change within the radiation sensitive filler by sending an energy wave to the radiation sensitive filler and capturing a signal emitted therefrom; and
    c) a control unit adapted for processing said captured signal and calculating a dose of ionizing radiation previously or simultaneously received by each part of the volume of the radiation sensitive filler taking said signal into account.

2. The system according to claim 1, wherein the radiation sensitive filler comprises a suspension of superheated droplets.

3. The system according to claim 2, wherein the superheated droplets are encapsulated by a polymeric shell.

4. The system according to claim 2, wherein the superheated droplets are in a stable state and the droplets are adapted for re-condensing when switching the radiation source off such as to spontaneously reset said physical and/or chemical change of said radiation sensitive filler.

5. The system according to claim 2, wherein the superheated droplets are in a metastable state.

6. The system according to claim 1, wherein the radiation sensitive filler comprises a suspension of gas-filled microbubbles.

7. The system according to claim 1, wherein the detector system is a CT scanner.

8. The system according to claim 1, wherein the detector system is an acoustic readout system.

9. A method for measuring a dose of ionizing irradiation received by a pre-determined body part during a radiotherapy treatment, said method comprising:
    a) sending an energy wave to a viscous or semi-solid radiation sensitive filler, the viscous or semi-solid radiation sensitive filler being pre-injected between said predetermined body part and a tissue to be protected from radiation, said radiation sensitive filler being adapted for undergoing a measurable physical and/or chemical change under the influence of ionizing irradiation and for substantially preserving, during said radiotherapy treatment, its initial morphology in order to minimize dose to the tissue to be protected from radiation, the initial morphology being determined by the shape and volume of said radiation sensitive filler after being pre-injected between said predetermined part of the body and said tissue to be protected;

b) capturing a signal emitted by the radiation sensitive medium elicited by said energy wave, whereby said emitted signal has characteristics that reflect said physical and/or chemical change; and c) processing said captured signal and calculating the dose of ionizing irradiation previously or simultaneously received by each part of the radiation sensitive filler taking said signal into account.

10. A radiation sensitive filler for measuring a dose of ionizing irradiation received by a pre-determined body part during a radiotherapy treatment, said radiation sensitive filler being a viscous or semi-solid radiation sensitive filler adapted for being injected between said predetermined body part and a tissue to be protected from radiation, wherein the radiation sensitive filler is adapted for undergoing a measurable physical and/or chemical change under the influence of ionizing irradiation and for substantially preserving, during said radiotherapy treatment, its initial morphology in order to minimize dose to the tissue to be protected from radiation, the initial morphology being determined by the shape and volume of said radiation sensitive filler upon injection between said predetermined part of the body and said tissue to be protected, said radiation sensitive filler furthermore being adapted for emitting a signal when elicited by an energy wave, whereby said emitted signal has characteristics that reflect said physical and/or chemical change.

11. The radiation sensitive filler according to claim 10, comprising a viscous medium having liquid droplets dispersed therein and/or comprising a suspension of gas-filled microbubbles.

12. The radiation sensitive filler according to claim 10, wherein said radiation sensitive filler is biocompatible and biodegradable.

13. The radiation sensitive filler according to claim 10, wherein said radiation sensitive filler is adapted to preserve its initial morphology in order to minimize dose to the rectum for radiotherapy of the prostate or of the cervix.

14. The radiation sensitive filler according to claim 10, wherein said radiation sensitive filler is adapted to preserve its initial morphology in order to minimize dose to a bowel and/or at least one kidney for paraspinal, sacral or pelvic radiotherapy.

* * * * *